United States Patent [19]

Dworkin et al.

[11] 4,104,292
[45] Aug. 1, 1978

[54] METHOD FOR PREPARING ORGANOTIN COMPOUNDS

[75] Inventors: Robert D. Dworkin, Old Bridge; Adam J. Ejk, Piscataway, both of N.J.

[73] Assignee: M&T Chemicals Inc., Stamford, Conn.

[21] Appl. No.: 738,183

[22] Filed: Nov. 2, 1976

[51] Int. Cl.² .................................................. C07F 7/22
[52] U.S. Cl. .............................. 260/429.7; 260/399; 260/410; 260/410.6
[58] Field of Search ................... 260/429.7, 410, 410.6, 260/399

[56] References Cited

U.S. PATENT DOCUMENTS

| 2,832,750 | 4/1958 | Weinberg et al. | 260/429.7 |
| 2,870,182 | 1/1959 | Leistner et al. | 260/429.7 |
| 2,885,415 | 5/1959 | Ramsden | 260/429.7 |
| 3,931,263 | 1/1976 | Molt | 260/429.7 |
| 3,979,359 | 9/1976 | Kugele et al. | 260/410.6 X |

Primary Examiner—Helen M. S. Sneed
Attorney, Agent, or Firm—Kenneth G. Wheeless; Robert Spector

[57] ABSTRACT

Organotin derivatives of mercaptoalcohol esters corresponding to the general formula

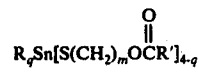

$$R_qSn[S(CH_2)_mOCR']_{4-q}$$

wherein R and R' are hydrocarbon, m is 2 or 3 and q is 1 or 2 are prepared by reacting a mercaptoalcohol of the formula $HS(CH_2)_mOH$ with a diorganotin oxide, organostannoic acid or an anhydride of said acid in an aqueous medium and subsequently esterifying the reaction product with the desired carboxylic acid, R'COOH, or an ester thereof. The present method offers advantages over the prior art, which teaches reacting an esterified mercaptoalcohol with an organotin compound. Compounds wherein R' is n-heptyl are unique in that they do not exhibit the disagreeable odors that characterize this class of compounds.

17 Claims, No Drawings

METHOD FOR PREPARING ORGANOTIN COMPOUNDS

BACKGROUND

This invention relates to a method for preparing a particular class of organotin compounds. This invention further relates to a method for preparing organotin derivatives of mercaptoalcohol esters which offers advantages with respect to known methods for preparing this class of organotin compounds.

U.S. Pat. No. 2,870,182 discloses compounds of the general formula $R_nSnA_{4-n}$ wherein R represents one of a specified group of hydrocarbon radicals, n is 1, 2 or 3 and A represents the residue obtained following removal of the hydrogen atom from the —SH group of a mercaptoalcohol ester. The patent further discloses that compounds corresponding to the foregoing formula can be prepared by first reacting the mercaptoalcohol with a carboxylic acid in the presence of a suitable esterification catalyst and subsequently reacting the resultant ester with an organotin halide, oxide or with an organostannoic acid. This preparative method is less than desirable for a number of reasons. Firstly, formation of the mercaptoalcohol ester is an equilibrium reaction which almost always requires an acidic catalyst and removal of water during the reaction to obtain a useful yield of the desired product within a reasonable length of time. The acid catalyst may promote a number of undesirable side reactions, including polymerization of the mercaptoalcohol. The polymer may contain end groups that will subsequently react with the organotin compound, however the product is not nearly so effective as the desired monomeric ester derivative in a number of applications, including stabilization of vinyl chloride polymers. A second undesirable feature of the aforementioned prior art method is that removal of water is necessary during preparation of the ester and during reaction of the ester with the organotin compound. Removal of water requires heating, which not only increases processing costs due to the additional energy input, but can result in larger amounts of by-products from side reactions. In addition, a considerable amount of mercaptoalcohol is often removed together with the water, thereby necessitating use of a stoichiometric excess of this reagent. It has now been found that the disadvantages inherent in the prior art method can be avoided if the mercaptoalcohol is first reacted with the organotin compound and then esterified. Reactions of organotin halides and oxides with both mercaptans and alcohols are reported in the chemical literature. One would therefore expect to obtain a mixture of at least two products, one of which contains tin-oxygen bonds and a second compound containing tin-sulfur bonds. Surprisingly, under the conditions disclosed hereinafter only the mercaptide (—SH) portion of the mercaptoalcohol reacts with the organotin compound. The hydroxyl portion of the molecule remains available for subsequent esterification with a carboxylic acid or ester thereof.

SUMMARY OF THE INVENTION

This invention provides a method for preparing organotin compounds of the general formula

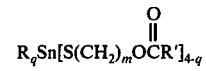

wherein R and R' are individually selected from the group consisting of alkyl containing from 1 to 20 carbon atoms, cycloalkyl, aryl, alkaryl and aralkyl, m represents the integer 2 or 3 and q represents the integer 1 or 2, said method consisting essentially of the following sequence of steps:
(1) reacting 2-mercaptoethanol or 3-mercaptopropanol with a stoichiometric amount of (a) a diorganotin oxide of the formula $R_2SnO$ when q is 2, or (b) an organostannoic acid of the formula RSnOOH or an anhydride of said acid when q is 1;
(2) reacting the product obtained thereby with a stoichiometric amount of a carboxylic acid, R'COOH, or an ester of said acid, represented by the formula R'COOR'', wherein R'' is alkyl and contains from 1 to 20 carbon atoms;
(3) removing the by-product water or said alcohol R''OH from the reaction mixture and isolating said organotin compound. Optionally the alcohol R''OH is retained in the reaction mixture when R'' contains more than 10 carbon atoms.

Alternatively the organotin oxide can be replaced by the corresponding organotin halide, $R_qSnX_{4-q}$ wherein X is chlorine, bromine or iodine and q is 1 or 2. The organotin halide is reacted with an aqueous solution of an inorganic base. The number of equivalent weights of base present is at least equal to the number of moles of X atoms. This reaction yields the corresponding diorganotin oxide or organostannoic acid, which is then reacted with the mercaptoalcohol as described in the foregoing specification.

DETAILED DESCRIPTION OF THE INVENTION

The first step of the present method for preparing organotin derivatives of specified mercaptoalcohol esters comprises reacting a diorganotin oxide, an organothiostannoic acid or an anhydride of said acid with 2-mercaptoethanol or 3-mercaptopropanol. The organotin compound can either be prepared and isolated prior to being reacted with the mercaptoalcohol or it can be formed in situ by reaction of the corresponding organotin halide with an aqueous solution of an inorganic base. The organotin halides are represented by the general formula $R_qSnX_{4-q}$. The terms R, X and q have previously been defined. The quantity of base employed is sufficient to react with all of the halogen atoms present in the organotin halide. It will be understood that three equivalent weights of base are required for each mole of a monoorganotin trihalide. Two equivalent weights of base are employed for each mole of a diorganotin dihalide.

As disclosed in the preceding specification, the term "X" in the foregoing formulae represents chlorine, bromine or iodine and "R" represents alkyl containing from 1 to 20 carbon atoms, cycloalkyl, aryl, alkaryl or aralkyl. When R is alkyl it can be methyl, ethyl, n-propyl, iso-propyl or any higher homolog containing up to 20 carbon atoms. Suitable cycloalkyl radicals include, for example, cyclopropyl, cyclobutyl, cyclohexyl and cyclooctyl. When R is aryl it is preferably phenyl but may also represent naphthyl, anthrecenyl or biphenyl. Suitable aralkyl radicals include, for example, benzyl and β-phenylethyl. When R is alkaryl it can be, for example, one of the isomeric tolyl, xylyl or other alkyl-substituted phenyl radicals.

The base employed can be ammonium hydroxide, an alkali metal hydroxide, such as sodium hydroxide or an alkaline earth metal hydroxide, for example calcium hydroxide. A corresponding alkoxide, such as sodium methoxide, can be employed in place of a hydroxide.

The reaction between the halogen atoms of the organotin halide and the base is rapid at ambient temperature and is often highly exothermic. The organotin halide should therefore be gradually added to the aqueous base solution while the reaction mixture is stirred and cooled to prevent localized overheating. It may be desirable to continue stirring the reaction mixture after all of the organotin halide has been added in order to improve heat transfer and thereby increase the rate of cooling.

Irrespective of how it is obtained, the aqueous suspension containing a diorganotin oxide or an organostannoic acid is reacted with the desired mercaptoalcohol. The rate of this reaction is considerably slower than the rate at which organotin halides react with bases. It may therefore be necessary to heat the mixture to from 40° to 100° C. to complete the reaction in a reasonable length of time, usually from 5 to 60 minutes. Three moles of mercaptoalcohol are added for each mole of a monoorganotin compound. A diorganotin compound requires 2 moles of mercaptoalcohol per mole of organotin compound.

The most readily available mercaptoalcohols are 2-mercaptoethanol and 3-mercaptopropanol. These compounds are therefore preferred for use in the present method. Other known mercaptoalcohols, for example 4-mercapto-1-butanol, are equally suitable.

The reaction product of the diorganotin oxide or organostannoic acid and the mercaptoalcohol is esterified by addition of the desired carboxylic acid represented by the formula R'COOH or an ester thereof to the reaction mixture. Suitable acids contain from 2 to 20 carbon atoms and the hydrocarbon residue is alkyl, cycloalkyl, aryl, aralkyl or alkaryl as previously disclosed for the hydrocarbon portion or the organotin halide reactant. R' may contain one or more substituents including halogen, hydroxyl, alkoxy and nitro groups. In contrast to conventional esterification reactions, a stoichiometric excess of carboxylic acid is not required, nor is it necessary to add a catalyst. If an ester of the acid is employed, the alcohol residue contains from 1 to 20 carbon atoms. The more volatile alcohols containing between 1 and 4 carbon atoms are preferred, since these are readily removed by distillation.

If the final product is to be used as a stabilizer for halogenated polymers, it may be desirable that the alcohol residue of the aforementioned ester contain from 12 to 20 carbon atoms, since these alcohols function as lubricants and processing acids in the polymer formulation. In this instance, the alcohol would be isolated together with the final organotin compound.

Once the acid or ester has been added the aqueous phase of the reaction mixture is removed and discarded. In the event that a separation of liquid phases does not spontaneously occur at this point, it can be brought about by adjusting the pH of the reaction mixture to from 6.0 to 6.5 by the addition of a suitable base such as ammonium hydroxide. Once the aqueous phase is removed, the reaction mixture is heated to 100°-180° C. to effect the esterification or transesterification reaction while the by-product water, alcohol, or a mixture of water and esterifying alcohol is continuously removed using a suitable distillation apparatus. To minimize overheating and the accompanying product decomposition, the final portion of water is preferably removed under a reduced pressure that is usually equivalent to 10–100 mm. of mercury. Once all of the water has been removed the final liquid organotin compound remains in the reaction vessel. It may be necessary to filter the product to remove small amounts of solid materials. As previously disclosed, the product may also contain the aforementioned alcohol component R"OH in those instances when R" contains more than 10 carbon atoms.

The products obtained using the present method are useful for the same applications as other mono- and diorganotin compounds containing tin-sulfur bonds. The present compounds are particularly effective heat stabilizers for vinyl chloride polymers and other high molecular weight halogen-containing polymers. The stabilizers are conventionally employed at concentrations from 0.1 to 10% by weight. Organotin derivatives of mercaptoalcohol esters may also find use as antioxidants for a variety of materials. Compounds wherein R' of the foregoing formula is n-heptyl are unique in that they do not exhibit the disagreeable mercaptan type of odor characteristic of this class of compounds.

The following examples demonstrate preferred embodiments of the present method and, as such, should not be interpreted as limiting the scope of the accompanying claims.

EXAMPLE 1

Preparation of
Monobutyltin-S,S',S"-tris(2-mercaptoethyl caprylate)

A glass reactor equipped with a water-cooled condenser, mechanically driven stirrer and thermometer was charged with 28.2 (0.1 mole) of monobutyltin trichloride and 35 cc. of water. A 15.7 g. portion of concentrated (60% by weight) ammonium hydroxide solution was gradually added to the reactor over a period of 7 minutes. Stirring was continued throughout the course of the reaction. Five minutes following completion of the ammonium hydroxide addition 23.9 g. (0.3 mole) of 2-mercaptoethanol were added to the reactor in one portion. The contents of the reactor were then heated to 70° C. and the pH was adjusted to 6.5 by addition of ammonium hydroxide. A 43.3 g. portion of caprylic acid was then added to the reactor and the resultant mixture was heated to a temperature of 85° C., at which time the aqueous layer which formed was removed. The reactor was then equipped for distillation, purged with nitrogen and the contents heated to 140° C. for a period of 2½ hours. The light yellow liquid residue in the reactor was isolated by filtration and weighed 72.6 g., equivalent to a yield of 93% of the theoretical value. The distillate weighed 13.6 g. and did not have the disagreeable odor characteristic of mercaptoethanol derivatives.

EXAMPLE 2

Preparation of
Monobutyltin-S,S',S"-tris(2-mercaptoethyl oleate)
Using Prior Art Method A glass reactor equipped with a water-cooled condenser, mechanically driven stirrer and thermometer was charged with 58.7 g. (0.15 mole) of 2-mercaptoethyl oleate (as an impure mixture containing 86% by weight of the desired reactant) and 14.1 g. (0.05 mole) of monobutyltin trichloride. A mixture containing 9.1 g. (0.16 moles) of ammonium hydroxide and 10 cc. of water was gradually added to the reactor over a 10 minute period. Ten minutes following completion of the addition the contents of the reactor were heated to between 85° and 90° C. for 20 minutes. The aqueous phase of the reaction mixture was removed and discarded. Water was removed from the organic phase by heating it for 20 minutes at 120° C. under reduced pressure. The residual liquid was isolated by filtration and weighed 58.6 g. (87% yield).

This example demonstrates that the yield obtained using prior art methods are lower than those that can be achieved using the method of this invention. An additional advantage of the present method is that it does not require use of a preformed mercaptoalcohol ester.

EXAMPLE 3

Monobutyltin-S,S',S''-tris(2-mercaptoethyl oleate) by Ester Interchange

This example demonstrates that an ester can be used in place of the corresponding carboxylic acid to react with the intermediate product (an organotin derivative of 2-mercaptoethanol).

A glass reactor equipped with a water-cooled reflux condenser, mechanically driven agitator and thermometer was charged with 28.2 g. (0.1 mole) of butyltin trichloride and 35 cc. water. When the resultant mixture cooled to 30° C., 19.14 g. (0.33 mole) of ammonium hydroxide was gradually added during a 25 minute interval. The temperature of the reaction mixture rapidly increased to 45° C. The rate of addition was adjusted to maintain the temperature below 60° C. A 23.94 g. (0.3 mole) portion of 2-mercaptoethanol was then added all at once and the contents of the reactor were heated to 70° C., at which time the pH of the reaction mixture was adjusted to 6.5 by the addition of ammonium hydroxide. A 88.9 g. (0.3 mole) portion of methyl oleate was then added and the resultant mixture was heated to a temperature of 85° C. When this temperature was reached the aqueous phase of the 3-phase reaction mixture was removed and discarded. The two remaining layers were combined in a reactor equipped with a distillation apparatus. The contents of the reactor were heated to 140° C. for 3 hours and the distillate collected in a suitable receiver. The residue exhibited an infrared spectrum that was characteristic of the desired product (strong ester carbonyl absorption maximum at 5.75 μ; strong carbon-oxygen absorption peak at 8.5 μ; moderate absorption peak at 10.4 μ indicative of organotin oleate derivatives).

Organotin derivatives of mercaptoalcohol esters that are prepared in accordance with the present method can be reacted with organothiostannoic acids or diorganotin sulfides to form compounds containing two tin atoms joined by a sulfur bridge. Compounds of this type are disclosed in a copending patent application. The preparation of such a compound is described in the following example.

EXAMPLE 4

Preparation of bis[monobutyltin-S,S'-bis(2-mercaptoethyl caprylate)] sulfide

To 1037 g. (1.3 moles) of monobutyltin-S,S',S''-tris(2-mercaptoethyl caprylate) prepared as described in the preceding Example 2 was added 188.2 g. (0.667 mole) of butyltin trichloride and 400 cc. water. The resultant mixture was heated to 40° C., at which time 130.0 g. (1.0 mole) of sodium sulfide in flake form was gradually added over a 50 minute period. The reaction mixture was stirred during the addition and for 5 minutes thereafter, at which time the mixture was heated to 85° C. and the aqueous phase removed and discarded. The organic layer was returned to the reactor, which was equipped with a distillation apparatus. The contents of the reactor were heated under reduced pressure at a temperature of 95° C. for ½ hour, during which time 21.1 g. of distillate were collected. The pale yellow liquid remaining in the reactor was purified by filtration and weighed 1162 g., equivalent to a yield of 97.3%. The identity of the product was confirmed by infrared spectroscopy to be bis[monobutyltin-S,S'-bis(2-mercaptoethyl caprylate)] sulfide.

EXAMPLE 5

Evaluation of dibutyltin bis (2-mercaptoethyl oleate) as a stabilizer for a vinyl chloride homopolymer.

A formulation containing 100 parts by weight of a vinyl chloride homopolymer, 0.5 parts of a paraffin wax available as XL-165 and 2.0 parts of dibutyltin bis(2-mercaptoethyl oleate) was blended for five minutes on a two-roll differential speed mill heated to a temperature of 163° C. The sheet which formed was then removed from the mill and cut into squares measuring 1 inch (2.54 cm.) along each side. The color of the initial sheet was rated using the following scale:

7 — water-white
6 — off-white
5 — slight degree of yellowing
4 — definite yellow color
3 — deep yellow-brown
2 — deep brown
1 — dark brown or black The polymer samples were then placed in an oven maintained at a temperature of 202° C. Samples were withdrawn at 5 minute intervals and rated in accordance with the foregoing color scale.

A second set of samples prepared as described in the preceeding paragraph but omitting the organotin compound was employed as a control.

The color ratings exhibited by the stabilized and non-stabilized samples are summarized in the following table:

| Color rating following x minutes of heating: x = | 0 | 5 | 10 | 15 | 20 |
|---|---|---|---|---|---|
| Sample with stabilizer | 6 | 6 | 6− | 5 | 4 |
| Sample without stabilizer | 4 | 3+ | 3 | 2 | 1 |

The foregoing data demonstrate that diorganotin compounds prepared in accordance with the present method are effective heat stabilizers for vinyl chloride polymers.

What is claimed is:
1. A method for preparing an organotin compound of the general formula

wherein R and R' are individually selected from the group consisting of alkyl containing from 1 to 20 atoms, cycloalkyl, aryl, alkaryl and aralkyl, m represents the integer 2 or 3 and q represents the integer 1 or 2, said method consisting essentially of the following sequence of steps:
(1) combining 4-q moles of 2-mercaptoethanol or 3-mercaptopropanol for every one mole of an organostannoic acid, RSnOOH, when q is 1 or a diorganotin oxide, R₂SnO, when q is 2, and heating the resultant mixture at a temperature of from 40° to 100° C and for a period of time sufficient to substantially complete the reaction;
(2) combining the resultant product with a stoichiometric quantity of a carboxylic acid R'COOH, or an ester thereof, R'COOR", wherein R" is alkyl and contains from 1 to 20 carbon atoms, and subsequently removing the aqueous phase of the reaction mixture;
(3) heating the organic phase of said reaction mixture to a temperature of from 100° to about 180° C and simultaneously removing any by-product water or any alcohol boiling at or below the temperature of the reaction mixture;
(4) removing the resultant organotin compound,

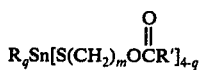

from the reaction vessel.

2. A method as set forth in claim 1 wherein R and R' are individually selected from the group consisting of radicals containing from 1 to 20 carbon atoms.

3. A method as set forth in claim 2 wherein R is butyl.

4. A method as set forth in claim 1 wherein said carboxylic acid is caprylic acid or pelargonic acid.

5. A method as set forth in claim 1 wherein m is 2.

6. A method as set forth in claim 1 wherein R" contains from 1 to 4 carbon atoms.

7. A method as set forth in claim 1 wherein the reaction between the mercaptoalcohol and the organotin compound is conducted in an aqueous medium.

8. A method as set forth in claim 1 wherein the product of step 1 is reacted with an ester of the formula R'COOR" wherein R" contains from 1 to 10 carbon atoms and the resultant alcohol R"OH is removed by distillation prior to isolating said organotin compound.

9. A method as set forth in claim 1 wherein the product of step 1 is reacted with an ester of the formula R'COOR" wherein R" contains from 10 to 20 carbon atoms and the resultant alcohol R"OH is isolated as a mixture with said organotin compound.

10. A method for preparing an organotin compound of the general formula

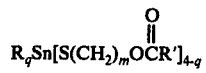

wherein R and R' are individually selected from the group consisting of alkyl containing from 1 to 20 carbon atoms, cycloalkyl, aryl, alkaryl and aralkyl, m is the integer 2 or 3 and q is the integer 1 or 2, said method consisting essentially of the following sequence of steps:
(1) reacting an organotin halide of the formula $R_qSnX_{4-q}$ wherein X is chlorine, bromine or iodine with (a) an aqueous solution of an inorganic base at ambient temperature, such that the number of equivalent weights of said base is at least equal to the number of moles of X atoms present in the reaction mixture;
(2) combining the resultant product with 4−q moles of 2-mercaptoethanol or 3-mercaptopropanol, and heating the mixture to a temperature of from 40° to 100° C and for a period of time sufficient to substantially complete said reaction;
(3) combining the resultant product with a stoichiometric quantity of a carboxylic acid R'COOH, or an ester thereof, R'COOR", wherein R" is alkyl and contains from 1 to 20 carbon atoms, and subsequently removing the aqueous phase of the reaction mixture;
(4) heating the organic phase of said reaction mixture to a temperature of from 100° to about 180° C and simultaneously removing any by-product water or any alcohol boiling at or below the temperature of the reaction mixture;
(5) removing the resultant organotin compound,

from the reaction vessel.

11. A method as set forth in claim 10 wherein R and R' are individually selected from the group consisting of alkyl radicals containing from 1 to 20 carbon atoms.

12. A method as set forth in claim 11 wherein R is butyl.

13. A method as set forth in claim 10 wherein said carboxylic acid is caprylic acid or pelargonic acid.

14. A method as set forth in claim 10 wherein m is 2.

15. A method as set forth in claim 10 wherein X is chlorine.

16. A method as set forth in claim 10 wherein the base reacted with the organotin halide is ammonium hydroxide.

17. A method as set forth in claim 10 wherein R" contains from 1 to 4 carbon atoms.

* * * * *